United States Patent [19]

Suzuki et al.

[11] Patent Number: 5,061,261
[45] Date of Patent: Oct. 29, 1991

[54] DISPOSABLE DIAPER

[75] Inventors: Migaku Suzuki, Kamakura; Satoshi Nozaki, Ehime; Takeshi Kudo, Kawanoe; Kazuaki Ohnishi, Kanoji, all of Japan

[73] Assignee: Uni-Charm Corporation, Ehimeken, Japan

[21] Appl. No.: 529,228

[22] Filed: May 25, 1990

[51] Int. Cl.⁵ .............................................. A61F 13/16
[52] U.S. Cl. ................................................. 604/385.2
[58] Field of Search .................... 604/385.2; 156/164, 156/201, 204

[56] References Cited

U.S. PATENT DOCUMENTS

| | | | |
|---|---|---|---|
| 4,425,128 | 1/1984 | Motomura | 604/385.2 |
| 4,636,207 | 1/1987 | Buell | 604/370 |
| 4,695,278 | 9/1987 | Lawson | 604/385.1 |
| 4,743,241 | 5/1988 | Igaue et al. | 604/385.2 |
| 4,795,454 | 1/1989 | Dragoo . | |
| 4,822,435 | 4/1989 | Igaue et al. . | |
| 4,834,740 | 5/1989 | Suzuki et al. . | |
| 4,904,251 | 2/1990 | Igaue et al. . | |

*Primary Examiner*—Randall L. Green
*Assistant Examiner*—G. Gualtieri
*Attorney, Agent, or Firm*—Dressler, Goldsmith, Shore, Stutker & Milnamow, Ltd.

[57] ABSTRACT

A disposable diaper includes a liquid-permeable topsheet, a liquid-barrier backsheet, and a liquid-absorptive core sandwiched between these two sheets. Side flaps extend from the two side edges of the core, and have elastic parts which are longitudinally stretchable. Side wings protrude from the two sides of the front and rear waist portions. Each side wing comprises a composite of a sweat-absorptive, air-permeable layer, and a liquid-barrier, air-permeable layer.

7 Claims, 2 Drawing Sheets

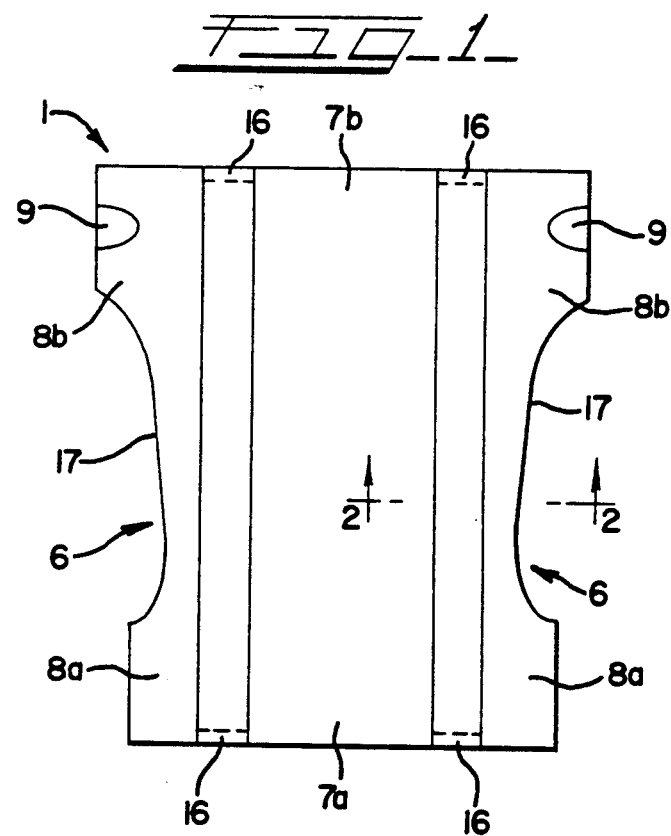
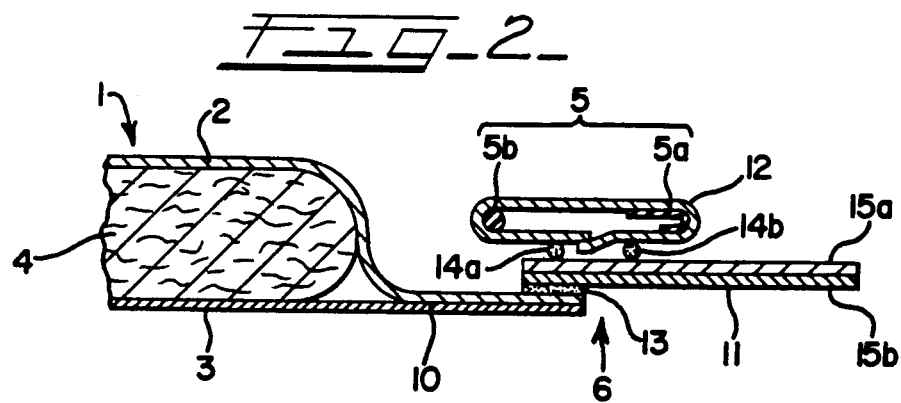

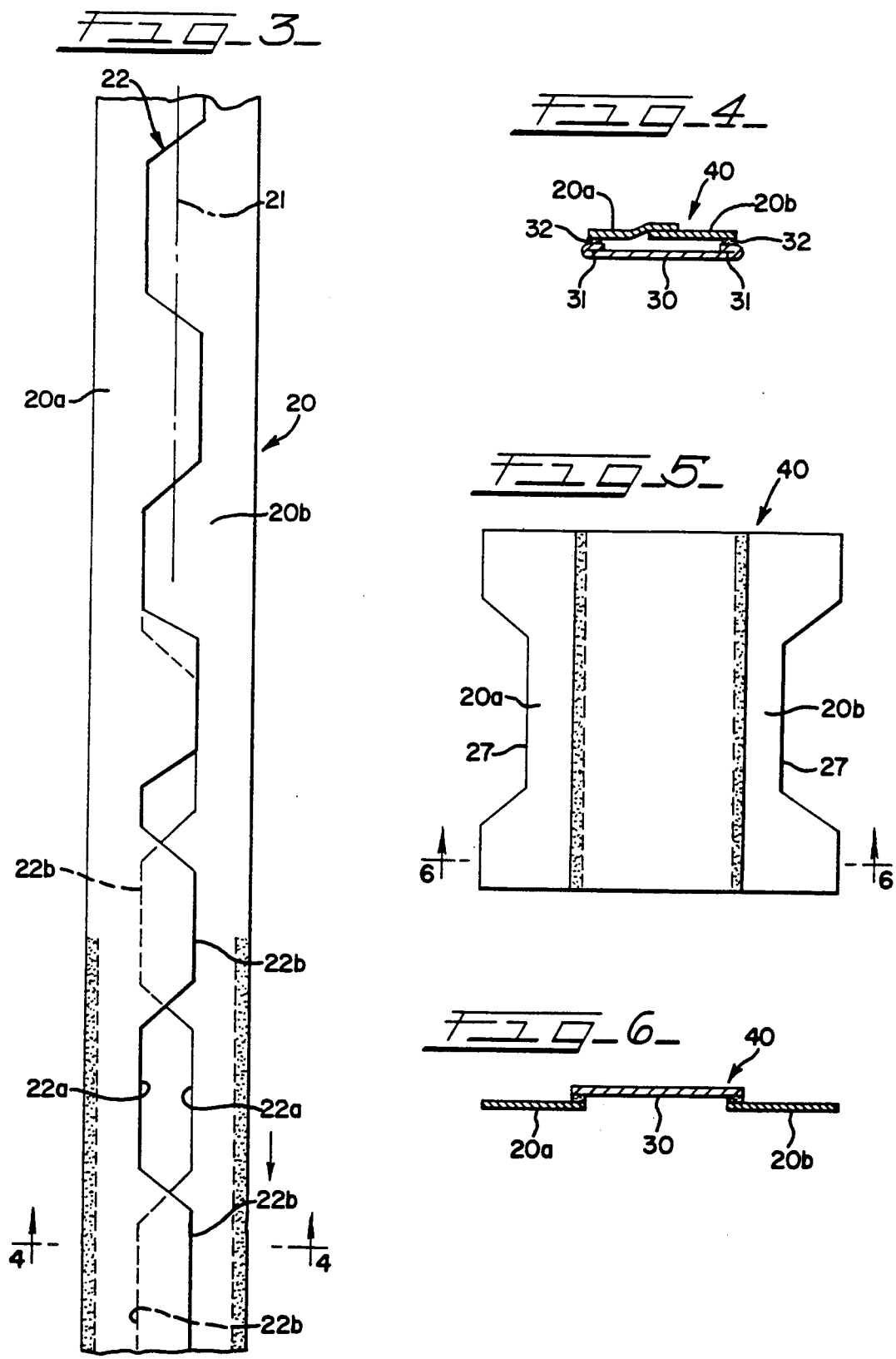

5,061,261

DISPOSABLE DIAPER

TECHNICAL FIELD

This design concerns a type of disposable diaper that does not require a separate diaper cover. More specifically, it concerns a type of disposable diaper having side wings protruding from the transverse sides of the waist and with sweat-absorptive and air-permeable properties.

BACKGROUND OF THE INVENTION

For the conventional diapers of this type, the side wings protruding from the transverse side of the waist are usually formed as a part of the side flaps located at the two transverse sides of the diaper. Since the side flaps are made of a laminate consisting of a liquid-permeable top sheet and a liquid-barrier backsheet, the side flaps containing the side wings are not air permeable. This causes a warm dampness.

In recent years, an air-permeable plastic film has been used at said backsheet. However, since the front and back side wings are overlapped when the diaper is used, the air permeability is poor and warm dampness still exists. This disadvantage is particularly significant in the summer. Since a lot of sweat is generated on the skin of the wearer in the summer, the wearer feels uneasy when said topsheet is hydrophobic.

The purpose of this design is to overcome the disadvantage of the conventional scheme by providing a type of disposable diaper and the top layer of the side wings having sweat-absorptive and air permeable ability and with the back layer of the side wings having liquid-barrier and air-permeable ability.

SUMMARY OF THE INVENTION

In order to realize the aforementioned purpose, this design provides a type of disposable diaper consisting of a liquid-permeable topsheet in contact with the skin (of the wearer), a liquid-barrier backsheet not in contact with the skin, a liquid-absorptive core sandwiched between these two sheets, side flaps extending from the two side edges of the core and having elastic parts stretchable in the longitudinal direction, and side wings protruding from the two sides of the front and rear waist portions.

Said side wings are made of a top layer in contact with the skin and a back layer not in contact with the skin. Said top layer can absorb sweat and is air permeable. Said back layer is a liquid barrier but is air permeable.

In a preferable application status, said side flaps are made of the same materials as said side wings, and the side wings are formed as a part of the side flaps.

The other preferable application status will be explained in the following with reference to application examples.

BRIEF DESCRIPTION OF THE DRAWINGS

FIG. 1 is a developed plan view of the diaper of this design.

FIG. 2 is a cross-sectional view cut along line II—II in FIG. 1.

FIG. 3 is a plan view of the example for continuous formation of a portion of the side flaps.

FIG. 4 is a cross-sectional view cut along line IV—IV in FIG. 3.

FIG. 5 is a developed plan view of the composite web cut at the length of a single diaper formed in the formation process shown in FIG. 3.

FIG. 6 is a cross-sectional view cut along line VI—VI in FIG. 5.

DESCRIPTION OF THE PREFERRED EMBODIMENTS

In the following, the application examples of the diaper of this design will be explained with reference to figures.

As shown in FIGS. 1 and 2, diaper (1) is made of liquid-permeable topsheet (2) in contact with the skin, liquid-barrier backsheet (3) not in contact with the skin, liquid-absorptive core (4) sandwiched between two sheets (2), (3), side flaps (6) which extend from and beyond the two side edges of the core and having elastic part (5) stretchable in the longitudinal direction, and side wings (8a), (8b) protruding from the two side edges of front and rear waist portion (7a), (7b). On side wing (8b) of rear waist portion (7b), pressing tape fastener (9) is mounted to fix on backsheet (3) of front waist (7a) when diaper (1) is assembled.

Each side flap (6) contains a first portion (10) made of top sheet (2) and backsheet (3) extending from the side edge of core (4) and bonded with each other, a second portion (11) which is bonded with the outer edge of the first portion via adhesive (13), and a third portion (12) which is bonded with the second portion via adhesives (14a), (14b) near the inner edge of the second portion.

Second portion (11) is made of a composite sheet consisting of top layer (15a) in contact with the skin and back layer (15b) not in contact with the skin. Top layer (15a) can absorb sweat and is air permeable. On the other hand, back layer (15b) is liquid-barrier but air-permeable. Top layer (15a) is made of sweat-absorptive nonwoven fabrics, such as spun-bond, melt-bond, melt-blown, or other nonwoven fabrics of polyester fibers with the fiber surfaces processed to become hydrophilic; nonwoven fabrics of polyester, polypropylene, and other hydrophobic fibers interwoven with said hydrophilic processed fibers, rayon, and other cellulose-series hydrophilic fibers using the water jet scheme; as well as the melt-bond nonwoven fabrics made of a mixture of the hydrophilic processed fibers or hydrophilic fibers and said hydrophobic fibers. It is preferred that the amount of the hydrophilic processed fibers of the hydrophic fibers with respect to the hydrophobic fibers be larger than 70%. Back layer (15b) is made of the spun-bond, melt-bond, or melt-blown nonwoven fabrics of polyester, polypropylene, etc., as well as polyethylene or other porous plastic film. Here, the porosity refers to the air permeability and [liquid] barrier properties acquired by slitting or punching the film. Top layer (15a) and back layer (15b) can be bonded using heating welding, ultrasonic welding or an adhesive (hot-melt type).

Third portion (12) is formed in a folded sleeve shape and is bonded with second portion (11). In addition, at two ends (16) in the longitudinal direction, it is bonded with first portion 10, and second portion (11). At the two side edges within the sleeve, elastic parts (5a), (5b) are attached while they are being stretched in the longitudinal direction. Elastic parts (5a), (5b) then contract, as a result, the two side edges of third portion (12) rise with respect to bonding portions (14a), (14b); the entire third portion (12) is deformed into a cross-sectional shape of U or V, with its two side edges pressing on the thighs of the wearer to prevent leakage of the body fluid. Preferably, third portion (12) is formed from the nonwoven fabrics of polyester, polypropylene, or other hydrophobic fibers. However, for this design, third portion (12) is not indispensable. It is also possible not to set a third portion (12), instead, an elastic part can be arranged along recession portion (17) of second portion (11) for press-sealing the thigh portion.

Recessed portion (17) arranged on side flap (6) can improve the fit of the diaper on the wearer's body. This recessed portion (17) can be realized by cutting off a portion of the sheet forming side flap (6). However, in order to reduce the cost of the diaper by reducing the amount of the starting material sheet, as shown in FIGS. 3–6, it is preferred that second portion (11) be formed as an integral part of side flap (6) and made to be bonded with topsheet (2) and/or backsheet (3).

One example of this scheme can be explained as follows. A continuous first web (20) is provided which comprises a laminate or composite of a sweat-absorptive and air-permeable layer, and a liquid barrier but air-permeable layer, such as described above for second portion (11). As shown in FIG. 3, continuous first web (20), which is to form second portion (11), has substantially parallel side edges, cutting lines (22) forming concave-convex portions via longitudinal central line (21) are cut by a roll cutter (not shown in the figure) in a periodically repeated manner in the longitudinal direction. In this way, first and second divided webs (20a), (20b) having concave edge portion (22a) and convex edge portion (22b) are formed, and at the same time, recessed portion 27 is formed. First division web (20a) is separated from second division web (20b), and it is deviated in the longitudinal direction by a pitch of (1/2)n (here, n is an odd number) with respect to second division web (20b). Concave edge portions (22a) and convex edge portions (22b) of first and second division webs (20a), (20b) are opposed and matched to each other.

On the other hand, for second web (30) to be used to form topsheet (2) or backsheet (3), its two sides are folded back to the upper surface; adhesive (32) is coated on fold-back portion (31) and it is positioned on the lower surface of first and second division webs (20a), (20b) matched with each other as pointed out above. As shown in FIG. 4, the outer edges of first and second division webs (20a), (20b) and the fold-back portions (31) of second web (30) are bonded with adhesive (32). In this way, continuous composite web (40), is formed from first and second division webs (20a), (20b) and second web (30). As shown in FIGS. 5 and 6, for composite web 40, first and second division webs (20a), (20b) are developed outwards and combined with the other structural parts of the diaper, followed by cutting at the prescribed portion.

EFFECTS OF THE DESIGN

For the diaper of this design, the top layer of the side wings protruding from the two side edges of the side flaps in contact with the skin can absorb sweat and are air permeable; on the other hand, the back layer not in contact with the skin is a liquid barrier but is air permeable. When the diaper is worn, the overlapped front and rear side wings in contact with the skin are still air permeable. In this way, the warm dampness can be significantly suppressed, the sweat can be absorbed, and the body fluid reaching the side wing region cannot leak out.

What is claimed is:

1. A disposable diaper comprising:
   a liquid-permeable topsheet (2) for contact with the skin of the wearer;
   a liquid barrier backsheet (3);
   a liquid absorptive core (4) sandwiched between the topsheet and the backsheet; and
   a pair of elasticized side flaps (6) extending longitudinally of said diaper at respective opposite side edges thereof,
   each said side flap (6) including portions of said topsheet and said backsheet which extend from a respective side edge of said absorbent core, and elastic means (5) extending longitudinally of said diaper generally at respective side edges of said topsheet and said backsheet of said side flap for elastically contracting said side flap,
   each said side flap further comprising a side wing extending laterally from the respective elastic means and from the side edges of said topsheet and said backsheet of said side flap, each said side wing extending laterally of at least one of front and rear waist portions of said diaper,
   each of said side wings comprising a composite two-layer sheet, including an air-permeable, sweat-absorptive top layer for contact with the skin of the wearer, and an air-permeable, liquid barrier back layer.

2. A disposable diaper in accordance with claim 1, wherein,
   each said side wing is joined with bond means (13) to at least one of said side edges of said topsheet and said backsheet of said side flap.

3. A disposable diaper in accordance with claim 2, wherein
   said bond means comprises adhesive.

4. A disposable diaper in accordance with claim 1, wherein
   each said elastic means comprises an outer covering sleeve (12), and at least one elastic element extending within said outer covering sleeve.

5. A disposable diaper in accordance with claim 4, wherein
   said outer covering sleeve of each said elastic means is bonded with bond means at the respective side edges of said topsheet and said backsheet,
   each said elastic means including a pair of elastic elements (5a, 5b) extending generally along opposite sides of the respective bond means for said covering sleeve, so that contaction of said elastic elements results in said covering sleeve having a generally U-shaped cross-sectional shape.

6. A disposable diaper in accordance with claim 1, wherein
   said top layer of each said side wing comprises nonwoven fabric comprising at least 70 percent hydrophilic fibers.

7. A disposable diaper in accordance with claim 1, wherein
   said back layer of each said side wing comprises hydrophobic nonwoven fabric.

* * * * *